United States Patent
Doron et al.

(10) Patent No.: US 8,626,295 B2
(45) Date of Patent: Jan. 7, 2014

(54) ULTRASONIC TRANSDUCER FOR BI-DIRECTIONAL WIRELESS COMMUNICATION

(75) Inventors: Eyal Doron, Kiriat-Yam (IL); Bin Mi, Plymouth, MN (US); Abhi V. Chavan, Maple Grove, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 491 days.

(21) Appl. No.: 13/038,754

(22) Filed: Mar. 2, 2011

(65) Prior Publication Data

US 2011/0218594 A1    Sep. 8, 2011

Related U.S. Application Data

(60) Provisional application No. 61/310,474, filed on Mar. 4, 2010.

(51) Int. Cl.
*A61N 1/08* (2006.01)

(52) U.S. Cl.
USPC .............................................. 607/32; 607/60

(58) Field of Classification Search
USPC ................................................... 607/32, 60
See application file for complete search history.

(56) References Cited

U.S. PATENT DOCUMENTS

| | | | |
|---|---|---|---|
| 3,612,921 A | 10/1971 | Springate | |
| 6,140,740 A | 10/2000 | Porat et al. | |
| 7,522,962 B1 | 4/2009 | Doron et al. | |
| 7,566,308 B2 | 7/2009 | Stahmann | |
| 7,580,750 B2 | 8/2009 | Doron et al. | |
| 7,617,001 B2 | 11/2009 | Penner et al. | |
| 8,082,041 B1 * | 12/2011 | Radziemski | 607/61 |
| 2004/0204744 A1 | 10/2004 | Penner et al. | |
| 2006/0009818 A1 | 1/2006 | Von Arx et al. | |
| 2006/0149329 A1 | 7/2006 | Penner | |
| 2007/0088221 A1 | 4/2007 | Stahmann | |
| 2008/0021509 A1 | 1/2008 | Mi et al. | |
| 2008/0243210 A1 | 10/2008 | Doron et al. | |
| 2009/0326609 A1 | 12/2009 | Doron | |
| 2010/0004718 A1 | 1/2010 | Doron et al. | |

* cited by examiner

*Primary Examiner* — Carl H Layno
*Assistant Examiner* — Natasha Patel
(74) *Attorney, Agent, or Firm* — Schwegman Lundberg & Woessner, P.A.

(57) ABSTRACT

A piezoelectric element within an external ultrasonic transducer assembly can be used for wireless communication of data between an implantable device and the external ultrasonic transducer assembly such as using ultrasonic energy coupled to a flexible portion of a housing of the transducer assembly. The flexible portion can be configured to contact skin of a body containing the implantable device. The transducer assembly can be configured to respectively transmit or receive ultrasonic energy using at least partially overlapping respective ranges of resonant frequencies.

20 Claims, 6 Drawing Sheets

ULTRASONIC TRANSDUCER FOR BI-DIRECTIONAL WIRELESS COMMUNICATION

CROSS-REFERENCE TO RELATED APPLICATIONS

This application claims the benefit under 35 U.S.C. 119(e) to Doron et al., U.S. Provisional Patent Application Ser. No. 61/310,474, entitled "Ultrasonic Transducer for Bi-Directional Wireless Communication", which is hereby incorporated by reference herein in its entirety.

BACKGROUND

Implantable medical devices (IMDs) can perform a variety of diagnostic or therapeutic functions. An IMD can include one or more cardiac function management features, such as to monitor the heart or to provide electrical stimulation to a heart or to the nervous system, such as to diagnose or treat a subject, such as one or more electrical or mechanical abnormalities of the heart. Examples of IMDs can include pacemakers, automatic implantable cardioverter-defibrillators (ICDs), cardiac resynchronization therapy (CRT) devices, implantable monitors, neuromodulation devices (e.g., deep brain stimulators, or other neural stimulators), cochlear implants, or drug pumps, among others. IMDs can include a telemetry circuit and an antenna, coupled to the telemetry circuit, such as to provide magnetic coupling between the IMD and one or more other devices to provide wireless communication (e.g., to send information, such as physiological or other information, from the implantable medical device to the external device, or to receive information, such as programming instructions, at the implantable medical device from the external device).

Magnetic coupling can be used to provide short-range (e.g., centimeters) communication between an implantable medical device implanted in a body and an external device, or between an implantable medical device outside of the body and an external device. Magnetic coupling communication largely relies on near-field coupling, where the field distribution is highly dependent upon the distance between and relative orientations of the transmitting and receiving antennas. This limits the effective range of wireless communication between the implantable medical device and the external device.

OVERVIEW

Implantable medical devices (IMDs) can include one or more telemetry circuits to transfer information wirelessly between an external device and the IMD, such as after the IMD is implanted within a patient. The information can include operating commands or parameters either provided by the external device to the IMD, or from the IMD to the external device. Information from the IMD can include information obtained from one or more sensors, information about a patient's status, diagnostic information from the IMD, or the like. Various transduction schemes can be used to wirelessly transfer the information. In an example, information can be transferred acoustically such as between one or more implantable assemblies, or between an implantable assembly and an external transducer assembly, such as included in a handheld assembly. For example, the external handheld assembly can include one or more acoustic transducers, such as to interrogate or program the IMD via transcutaneous coupling of acoustic energy, such as including ultrasonic frequencies.

A piezoelectric element within the external handheld assembly can be used for wireless communication of information between an implantable device and the external handheld assembly, such as using ultrasonic energy coupled to a flexible portion of a housing of the external transducer assembly. The flexible portion can be configured to contact skin of a subject's body containing the implantable device. The transducer assembly can be configured to transmit or receive ultrasonic energy, such as by using at least partially overlapping respective transmit and receive ranges of resonant frequencies.

Example 1 includes an ultrasonic transducer assembly, such as comprising a housing including a flexible portion, the flexible portion configured to contact skin of a body containing an implantable device, a piezoelectric element within the housing configured for wireless communication of data between the implantable device and the ultrasonic transducer assembly using ultrasonic energy coupled to the flexible portion of the housing, a matching circuit included at least partially within the housing. In Example 1, the matching circuit can be configured to provide energy to the piezoelectric element using a first resonant operating frequency range, and to receive energy from the piezoelectric element using a second resonant operating frequency range when the piezoelectric element is receiving ultrasonic energy, and the first and second resonant operating frequency ranges can be at least partially overlapping.

In Example 2, the subject matter of Example 1 optionally includes a piezoelectric element configured to operate in a voltage-driven mode when the piezoelectric element is providing ultrasonic energy, and the piezoelectric element is optionally configured to provide a charge output to drive a charge amplifier when the piezoelectric element is receiving ultrasonic energy.

In Example 3, the subject matter of any one or more of Examples 1-2 optionally includes a piezoelectric element configured to at least one of provide or receive the ultrasonic energy using a flexural vibration mode of the flexible portion of the housing.

In Example 4, the subject matter of any one or more of Examples 1-3 optionally includes a piezoelectric element including a circular footprint, and the flexural vibration mode of the flexible housing optionally includes a deformation component orthogonal to a face of the circular footprint.

In Example 5, the subject matter of any one or more of Examples 1-4 optionally includes first and second resonant operating frequency ranges that can each include a like frequency of determinable efficiency between 20 kHz and 800 kHz.

In Example 6, the subject matter of any one or more of Examples 1-5 optionally includes an ultrasonic transducer assembly including first and second resonant operating frequency ranges that can each include a like frequency of peak efficiency at about 40 kHz.

In Example 7, the subject matter of any one or more of Examples 1-6 optionally includes a housing comprising one of aluminum or stainless steel.

In Example 8, the subject matter of any one or more of Examples 1-7 optionally includes a housing including an insulating layer on the flexible portion.

In Example 9, the subject matter of any one or more of Examples 1-8 optionally includes an insulating layer located on an exterior face of the flexible portion.

In Example 10, the subject matter of any one or more of Examples 1-9 optionally includes an insulating layer configured to decrease an acoustic impedance mismatch between the ultrasonic transducer assembly and the body in contact with the flexible portion of the ultrasonic transducer assembly in one or more of the first or second resonant operating frequency ranges.

In Example 11, the subject matter of any one or more of Examples 1-10 optionally includes a portion of the housing that can be electrically coupled to a portion of the piezoelectric element and at least a portion of the housing can be electrically coupled to the matching circuit.

In Example 12, the subject matter of any one or more of Examples 1-11 optionally includes an insulating layer located on an interior face of the flexible portion, and the insulating portion can be configured to electrically isolate the flexible portion of the housing from the piezoelectric element.

Example 13 can include, or can optionally be combined with the subject matter of any one of Examples 1-12 to include providing or using an ultrasonic transducer assembly, including a matching circuit coupled to a piezoelectric element, for wireless communication of data between an implantable device within the body and the ultrasonic transducer assembly, the providing including using ultrasonic energy coupled between the piezoelectric element and the implantable device. Example 13 can include providing or using energy coupled through a matching circuit to the piezoelectric element for transmission to the implantable device using a first resonant operating frequency range, or providing or using energy coupled from the piezoelectric element through the matching circuit using a second resonant operating frequency range when the piezoelectric element is receiving the ultrasonic energy. In Example 13, the first and second resonant operating frequency ranges can be at least partially overlapping.

In Example 14, the subject matter of any one or more of Examples 1-13 optionally includes at least one of providing a charge output when the piezoelectric element is receiving ultrasonic energy or providing ultrasonic energy using the piezoelectric element operating in a voltage-driven mode.

In Example 15, the subject matter of any one or more of Examples 1-14 optionally includes at least one of providing or receiving ultrasonic energy using a flexural vibration mode of a flexible portion of a housing coupled to the piezoelectric element.

In Example 16, the subject matter of any one or more of Examples 1-15 optionally includes using first and second resonant operating frequency ranges that can each include a like frequency of determinable efficiency between 20 kHz and 800 kHz.

In Example 17, the subject matter of any one or more of Examples 1-16 optionally includes using first and second resonant operating frequency ranges that can each include a like frequency of peak efficiency at about 40 kHz.

In Example 18, the subject matter of any one or more of Examples 1-17 optionally includes providing or using an insulating layer on a flexible portion of a housing of the ultrasonic transducer assembly. In Example 18, the flexible portion can be configured to contact skin of the body containing the implantable device.

In Example 19, the subject matter of any one or more of Examples 1-18 optionally includes providing or using the insulating layer including providing or using an insulating layer on an exterior face of the flexible portion of the housing, the body providing a first acoustic impedance and the ultrasonic transducer assembly providing a second acoustic impedance, and the providing or using the insulating layer optionally includes decreasing an impedance mismatch between the first and second acoustic impedances at least in part using the insulating layer.

In Example 20, the subject matter of any one or more of Examples 1-19 optionally includes providing an insulating layer on an interior face of the flexible portion of the housing can electrically isolate the piezoelectric element from the flexible portion of the housing.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, that acoustic telemetry using ultrasonic energy can be useful for communicating information, such as between one or more implantable medical devices (IMDs) and an external assembly. The external assembly can be sized and shaped to be handheld, such as including an ultrasound transducer configured for bi-directional communication with the one or more IMDs. In an example, the ultrasound transducer can include a hollow portion, such as to contain one or more components included in a matching circuit, and a piezoelectric element coupled to a flexible portion of the housing and to the matching circuit. The combination of the housing, matching circuit, and piezoelectric element can be used to provide an ultrasound transducer assembly having transmit and receive characteristics that can include like frequencies of determinable efficiency at or near resonance for both transmit and receive operation.

For example, the ultrasonic transducer can be operated in a voltage driven mode while transmitting using a first resonant frequency range, or the transducer can be coupled to a charge amplifier when receiving ultrasonic energy using a second resonant frequency range. The inventors have also recognized that at least some of the matching circuit components can be located within a hollow portion of the housing (e.g., a matching inductor nearby the piezoelectric element). Such a component location can both decrease the volume occupied by the ultrasonic transducer assembly, and can reduce mismatch between the transducer assembly and an amplifier or receiver. Locating at least some of the matching components within the housing can also reduce electrical interference susceptibility or emissions of the transducer assembly, since the housing can provide electrical shielding from other surrounding circuitry or interference sources. Also, locating at least some of the matching circuit components within the housing can reduce communication energy losses as compared to positioning the matching circuit further away from the piezoelectric element, or omitting the matching circuit.

Figure 1:
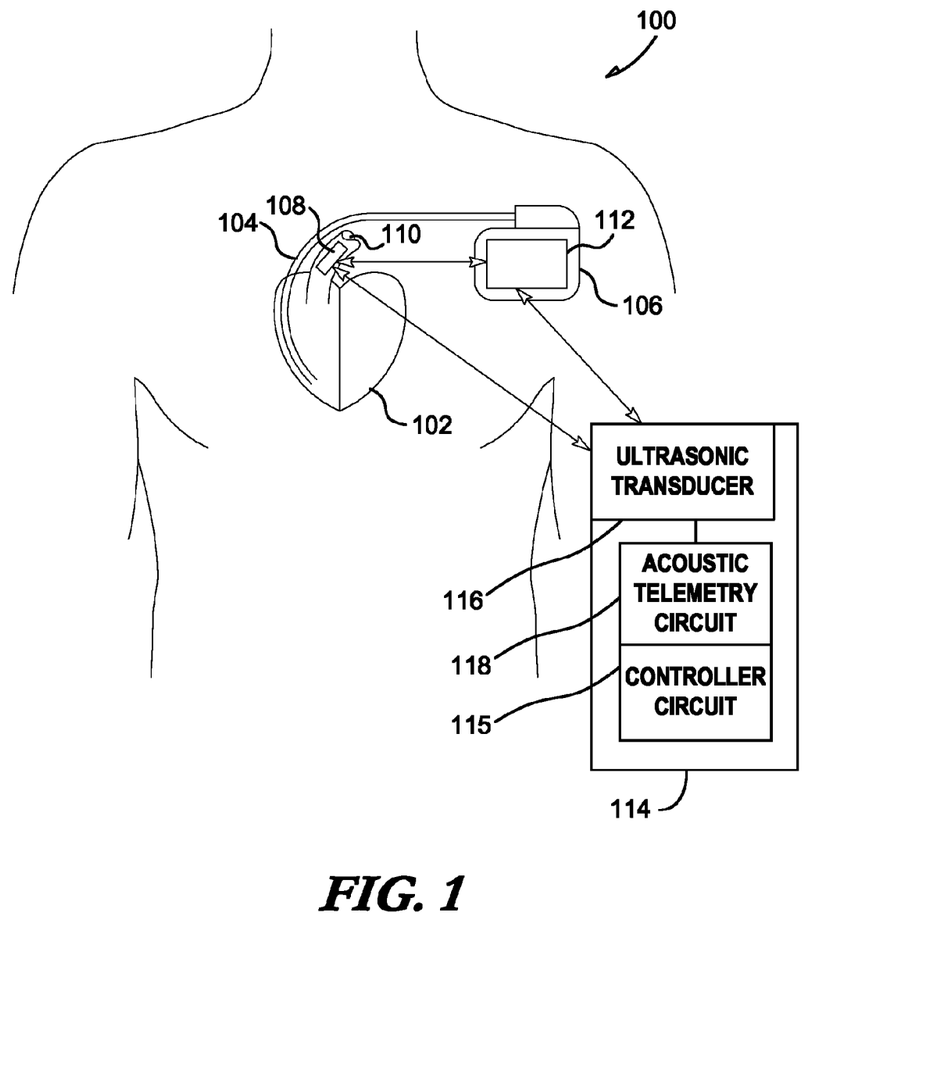
FIG. 1 illustrates generally an example of a system including implantable medical devices, and an external assembly including an ultrasonic transducer.

FIG. 1 illustrates generally an example of a system 100 that can include one or more implantable medical devices (IMDs), such as an implantable cardiac function management device (CFMD) 106, an implantable sensor 108, along with an external assembly 114 including an ultrasonic transducer (UT) 116. In an example, the CFMD 106 can include one or more leads, such as an intravascularly-deliverable lead 104, such as to provide one or more of a pacing therapy (e.g., bradycardia pacing, cardiac resynchronization pacing, or the like), a defibrillation countershock therapy (e.g., to terminate a tachyarrhythmia), a neural stimulation therapy, a drug delivery, or to provide remote sensing of electrical, mechanical, or chemical activity at one or more sites such as within or near a heart 102. In an example, the CFMD 106 can communicate with the implantable sensor 108, such as using one or more of an acoustic, a magnetic, a conductive, or an electromagnetic telemetry scheme, among others. In an example, the CFMD 106 can include an implantable ultrasonic transducer 112, such as positioned on or within a portion of the CFMD 106 housing.

In an example, the implantable sensor 108 can include an implantable pressure sensor such as located within a pulmonary artery 110, and the implantable sensor 108 can provide information about a pulmonary artery pressure to the CFMD 106, such as for use by the CFMD in determining a patient status, adjusting one or more therapy parameters, or for subsequent transmission to the external assembly 114 by the CFMD 106. An example of an intra-body ultrasonic telemetry system is discussed in U.S. Patent Application Publication No. 2006/0009818, entitled "METHOD AND APPARATUS OF ACOUSTIC COMMUNICATION FOR IMPLANTABLE MEDICAL DEVICE," filed on Jul. 9, 2004, assigned to Cardiac Pacemakers, Inc., which is incorporated herein by reference in its entirety, specifically including its discussion of modulation of acoustic energy for wireless acoustic transfer of information through a body, such as using one or more acoustic transducers coupled to a housing of an implantable medical device. Examples of an implantable PAP sensor such as the implantable sensor 108 are described in U.S. patent application Ser. No. 11/249,624, entitled "METHOD AND APPARATUS FOR PULMONARY ARTERY PRESSURE SIGNAL ISOLATION," filed on Oct. 13, 2005, assigned to Cardiac Pacemakers, Inc., which is incorporated herein by reference in its entirety, including its discussion of sensing information about pulmonary artery pressure (PAP) and transmitting information indicative of PAP to one or more other devices, such as using an acoustic communication scheme.

In an example, the external assembly 114 can use its UT 116 to communicate with one or more of the implantable sensor 108 or the CFMD 106, such as using ultrasonic energy coupled to or from the UT 116 through the body. In an example, a portion of the UT 116 can be positioned against the skin of the body containing the one or more IMDs, such as to allow transcutaneous coupling of ultrasonic acoustic energy from the transducer 116 through the skin and into the underlying tissue, or vice-versa. The external assembly 114 can include a controller circuit 115, such as coupled to an acoustic telemetry circuit 118 that can be capable of either driving the UT 116 or receiving energy from the UT 116. The controller circuit 115 can include one or more processors or memory circuits, such as for processing the information to be transmitted to or received from the one or more IMDs, or for interpreting or executing instructions causing the UT to transmit or receive information, among other things. For example, the controller circuit 115 can include a microprocessor or programmable logic device (PLD) such as including circuitry to provide instruction-set compatibility with one or more of an ARM™, an ARC™, a 68K, a PowerPC (PPC)™, an x86, or a Z80™ processor, or compatibility with one or more other processor architectures or families. In an example, the memory circuit can include one or more of a dynamic random access memory (DRAM), a static random access memory (SRAM), or one or more non-volatile memories such as a masked read-only memory (ROM), or an erasable-programmable read-only memory (EPROM). In an example, the memory circuit can include a FLASH memory circuit.

Figure 2:
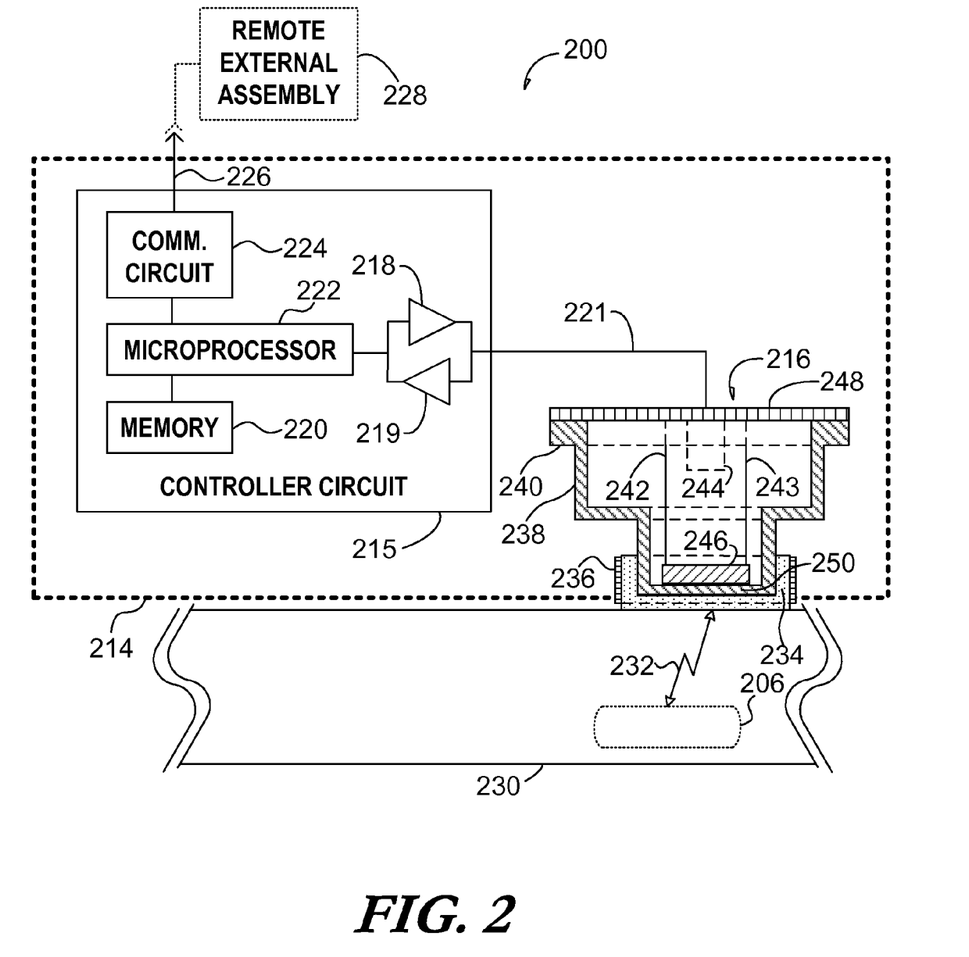
FIG. 2 illustrates generally an example of a system including an implantable medical device, a local external assembly, and a remote external assembly.

FIG. 2 illustrates generally an example of a system 200 that can include an implantable medical device 206, a local external assembly 214, and a remote external assembly 228. In an example, the local external assembly 214 can be similar to the external assembly 114 of FIG. 1, such as including a hand-held ultrasonic "reader" configured for use by a clinician, caregiver, or by a patient, such as to query the implantable device 206, configure the implantable device 206, or transfer information between the implantable device 206 and the local external assembly 214. In FIG. 2, the local external assembly 214 can include a controller circuit 215, and a coupling 221 to a UT assembly 216 contained at least partially within the local external assembly 214. In an example, the coupling 221 can include two or more conductors (e.g., leads, printed circuit board traces, or the like) such as connected to one or more components in a matching network, such as located within or near the UT 216.

The UT 216 can communicate with the implantable device 206 via an ultrasonic acoustic coupling 232, such as to transmit instructions or configuration information to the implantable device 206, or to receive information from the implantable device 206. For example, the ultrasonic acoustic coupling 232 can include transduction of an electrical signal including communication information into a sequence of pulses or other modulated acoustic energy, coupled through tissue, and then converted from acoustic energy back into a detectable or receivable electrical signal. In an example, the local external assembly 214 can retain information to be transmitted to or received from the implant 206, such as using a memory circuit 220.

In an example, the memory circuit 220 can include instructions, such as to be interpreted or executed by a microprocessor 222 included in the local external assembly, such as to control one or more of a transmit amplifier 218, a receiver 219, or another communication circuit 224, among other things. In an example, information stored in the memory circuit 220 can be transferred to the remote external assembly 228 using a communication link 226, such as a wireless communication link (e.g., using magnetic, electromagnetic, or optical communication, such as using an indoor wireless network or a cellular telephone network), or using a wired communication link (e.g., a link provided by one or more network adaptors, such as connected to the internet, or a public-switched telephone network (PSTN), or the like). For example, the local external assembly 214 can be used to retrieve information about a patient from the implant 206 (e.g., information obtained by a sensor such as discussed in FIG. 1), using the acoustic coupling 232, and the information can then be provided to the remote external assembly 228, such as using the communication link 226 and communication circuit 224. The remote external assembly 228 can include a nearby physician programmer, a desktop computer, a remote server or data repository, a cellular network basestation, a wireless network access point, or the like.

Figure 4:
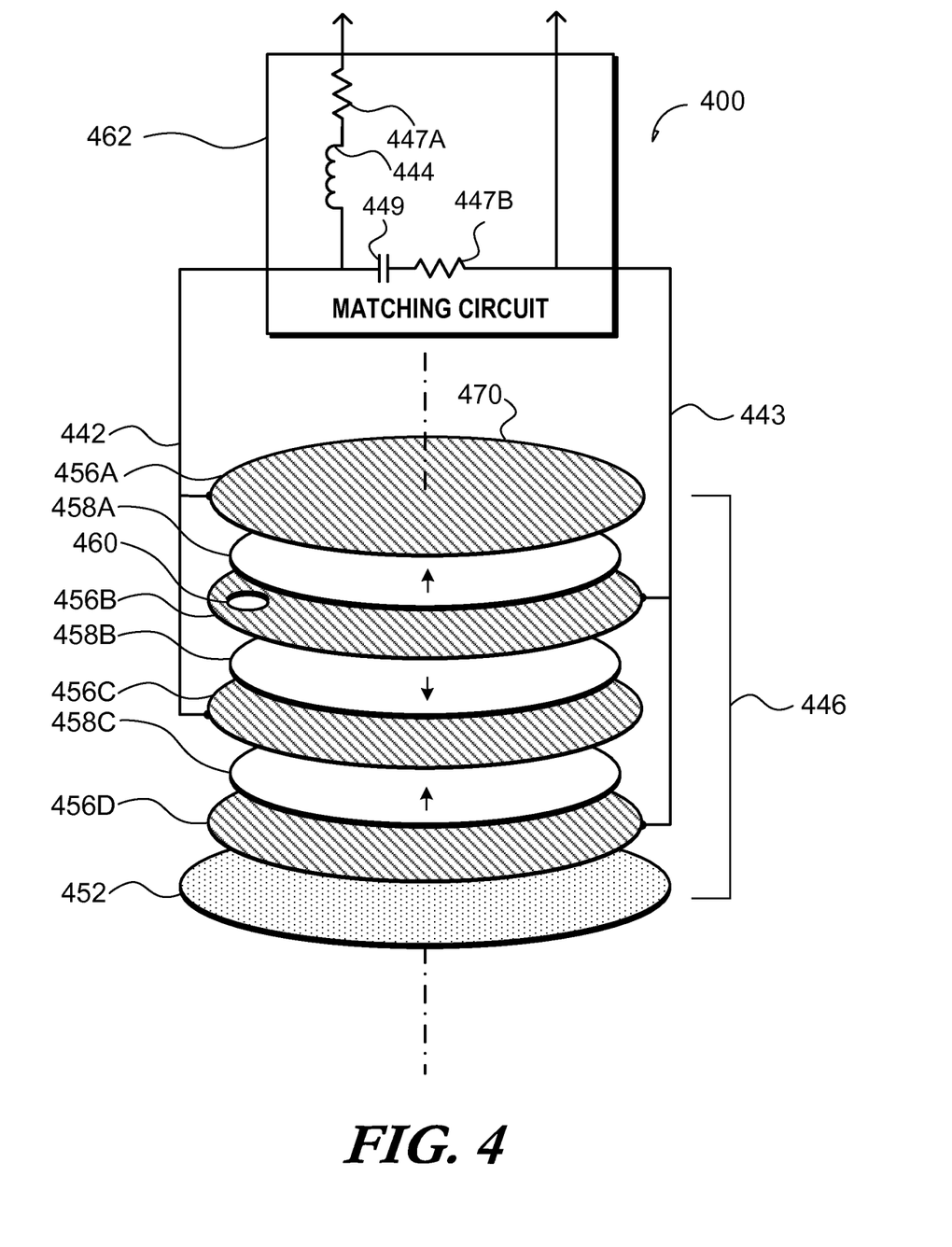
FIG. 4 illustrates generally an example of a piezoelectric element.

In FIG. 2, the UT 216 can be positioned against the skin of a patient 230. The ultrasonic transducer assembly 216 can include a housing 238 such as having a mounting flange 240, and a flexible portion 250 configured to contact the skin of the patient 230. In an example, the housing 238 can be metallic, such as a single-piece housing 238 machined out of a stainless steel or aluminum billet or casting, or drawn, rolled, formed, stamped, or the like, such as fabricated from one or more of a roll, a bar, or a sheet stock. Stainless steel can be desirable since it can provide structural rigidity for the housing 238 but can still be flexible enough to couple acoustic energy between the flexible portion 250 of the housing 238 and a piezoelectric element 246 contained within the housing and attached to the flexible portion 250. The piezoelectric element can include a stack of piezoelectric material layers (e.g. disc-shaped layers, or other footprint) sandwiched with electrode layers, such as shown in the example of FIG. 4. The piezoelectric element 246 can include a first lead 242, and a second lead 243, such as connected to a printed circuit board (PCB) assembly 248. In an example, the PCB assembly can include one or more components located inside a hollow portion of the housing 238 (e.g., an inductor 244 included as a portion of a matching circuit) such as connected to first and second leads 242-243.

Figure 3:
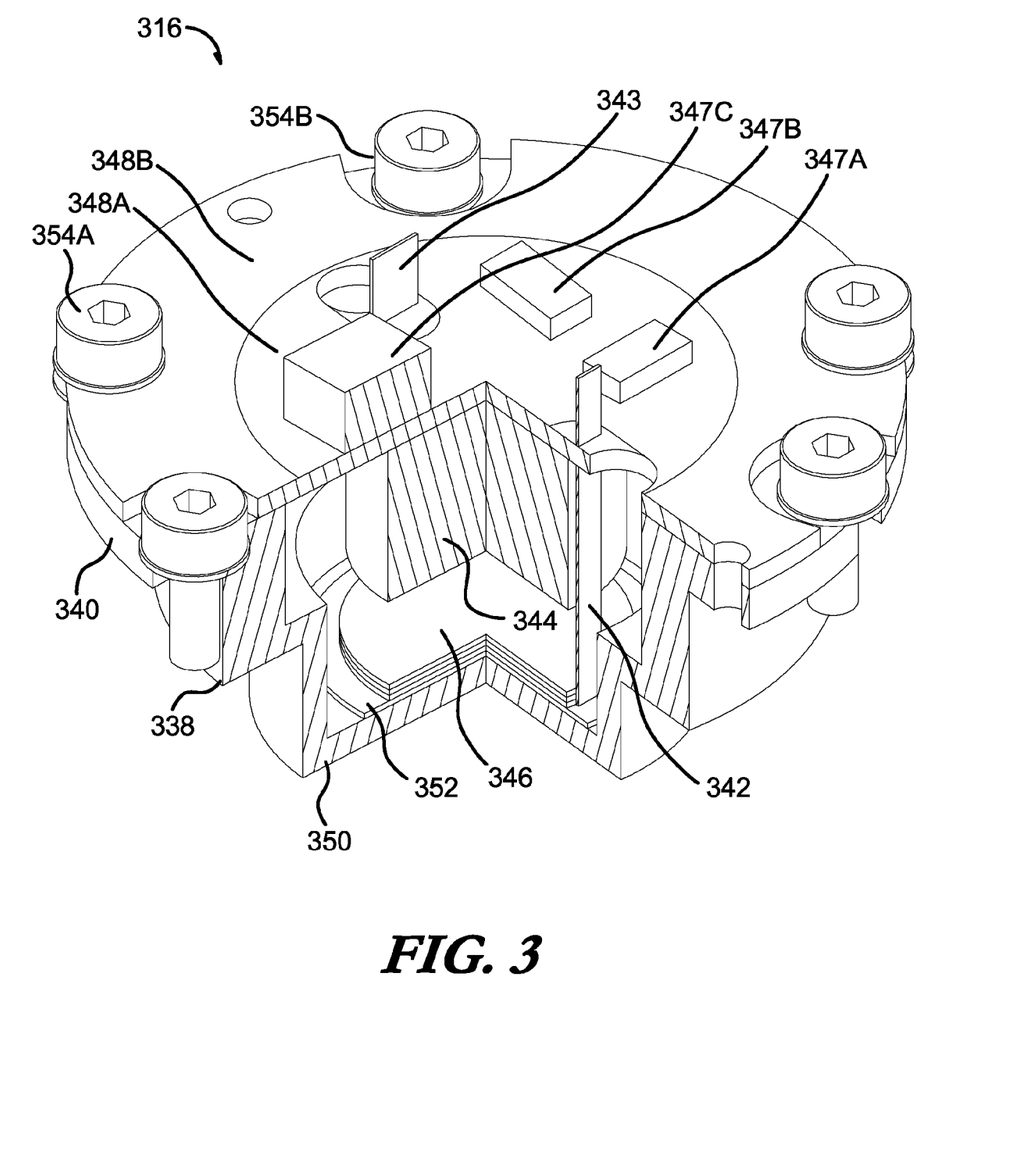
FIG. 3 illustrates generally an example of a cut-away view of an ultrasonic transducer assembly.
Figure 5A:
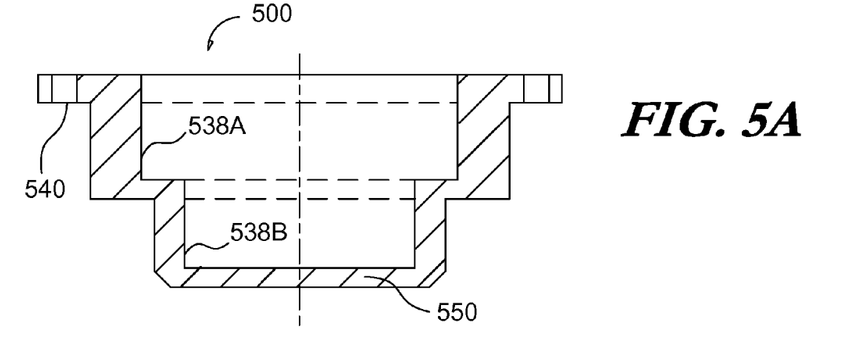
FIGS. 5A-C include illustrative examples of an ultrasonic transducer housing, a flexural model of a portion of the housing and a piezoelectric element, and a corresponding receiving sensitivity plot.
Figure 5B:
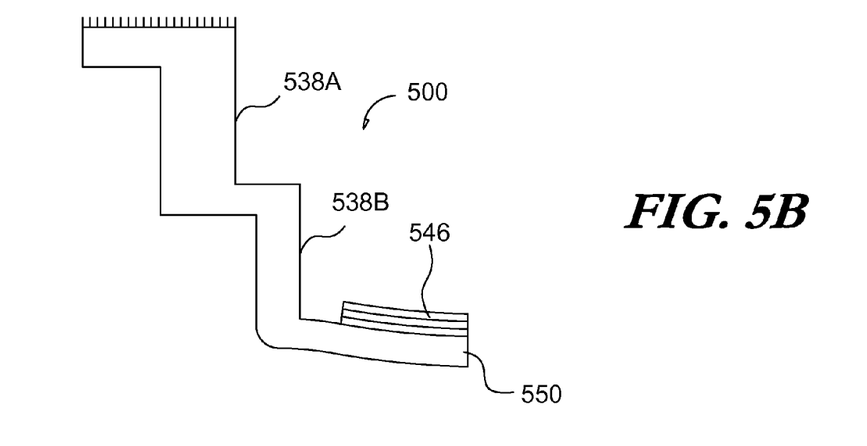

In an example, such as shown in FIG. 3 or 5, the housing 238 can have a circular footprint. The combination of the piezoelectric element 246 and the housing 238, including the flexible portion 250, can resonate at one or more specified ranges of frequencies, such as supporting a flexural mode of deformation of the flexible portion 250. The combination of the piezoelectric element 246 and the flexible portion 250 of the housing 238 can form a unimorph flexural transducer. In such a unimorph example, the flexible portion 250 of the housing 238 can include a circular footprint, and can vibrate using a flexural vibration mode including a deformation component orthogonal to the face of the circular footprint, such as shown in the illustrative example of FIG. 5B. For a unimorph flexural transducer, when the piezoelectric element 246 is driven, it attempts to expand or contract in a direction orthogonal to an applied electric field. Since the piezoelectric element 246 is attached to the flexible portion 250 of the housing 238, the expansion or contraction force is constrained and instead the flexible portion 250 flexes in relation to the applied voltage. Similarly, when the flexible portion 250 is mechanically excited by acoustic energy from outside the housing 238, such flexure can be coupled to the piezoelectric element 246 to provide an electrical signal.

In an example, the combination of the piezoelectric element 246 and the housing 238, including the flexible portion 250, can provide a resonant response for transmitting with peak efficiency when driven at or near a resonant frequency of between 20 kiloHertz (kHz) and 800 kHz, such as at about 40 kHz. The frequency of peak efficiency can correspond to a sensitivity at a frequency for which the UT 216 develops a higher pressure per volt of input stimulus as compared to other nearby frequencies. The UT 216 can be voltage-driven by a transmit amplifier 218 via the coupling 216A, such as using a first resonant operating frequency range. In an example, the first resonant operating frequency range can include the frequency of peak efficiency. In an example, when the UT 216 is operated in the voltage-driven mode at or near the frequency of peak efficiency, the power factor of the load presented by the combination of the matching circuit and the piezoelectric element 246 can be at or near unity.

Similarly, the combination of the piezoelectric element 246 and the housing 238, including the flexible portion 250, can provide a resonant response when receiving, including a frequency of peak sensitivity at between 20 kHz and 800 kHz, such as at around 40 kHz. In an example, the UT 216 can receive ultrasonic energy using a second resonant operating frequency range including the frequency of peak sensitivity, such as using a receiver 219 configured to operate in a charge-amplification mode (e.g., to convert a charge supplied by the piezoelectric element 246 to a voltage). The first and second resonant operating frequency ranges can at least partially overlap (e.g., when the element 246 is voltage-driven when transmitting or coupled to a charge amplifier when receiving), and the UT 216 can be used for bi-directional ultrasonic communication at like frequencies of determinable efficiency whether transmitting or receiving. The matching circuit, such as including the inductor 244, can be used to slightly broaden or spread the resonant receiving characteristic, or to enhance an efficiency of power coupling between the piezoelectric element 246 and the receiver 219. For example, the matching circuit can modify the admittance characteristic of the piezoelectric element 246 to provide a power factor at or near unity during transmit or receive modes of operation (e.g., an imaginary part of the admittance can oscillate around zero during mechanical resonance, enhancing efficiency as compared to omitting the matching circuit). In an example, the matching circuit can dampen or attenuate a transducer resonance, such as using a matching circuit pole located at a frequency slightly offset from a transducer resonant frequency.

In an example, the external assembly can include multiple UTs 216, or multiple piezoelectric elements 246 (e.g., four to six elements 246) within a UT 216, such as including one or more UTs 216 dedicated to receiving ultrasonic energy, or one or more UTs 216 dedicated to transmitting ultrasonic energy (e.g., such as including an array of UTs 216 at least partially exposed on the surface of the external assembly 214). In examples including multiple UTs 216, even if individual UTs are not used for bi-directional communication, the present inventors have also recognized that having a common UT 216 configuration for both transmit and receive can reduce production costs or complexity as compared to having individually customized UTs specifically for transmit operation, or for receive operation, but not both (e.g., the same or similar UT 216 configuration could be used regardless of whether its intended use is transmitting or receiving). In an example where the external assembly includes multiple UTs 216 or multiple piezoelectric elements 246, the multiple UTs 216 or multiple elements 246 can be selectively driven to permit directional focusing or control of the shape or direction of the acoustic wavefront generated by the UTs 216 or elements 246. Such focusing or steering can be used to overcome losses or scattering, such as due to air pockets in the communication path between one or more IMDs and the external assembly 214.

In FIG. 2, the housing 238 of the UT 216 can be conductively isolated from the skin of the patient 230, such as using an insulating layer 234 on the exterior surface of the housing 238, at least in the region near a face of the flexible portion 250 of the housing 238. In an example, the piezoelectric element 246 can include a piezoelectric layer electrically connected to the housing 238 on an interior face at or near the flexible portion 250 of the housing 238. The housing 238 can act as an electrode configured to couple voltage to the piezoelectric element 246 during transmission, or to provide a path for charge transfer from the piezoelectric element 246 when receiving acoustic energy. The insulating layer 234 can provide electrical isolation between the housing 238 and the patient 230, such as to prevent exposing the patient 230 to the voltages used to drive the piezoelectric element 246, such as when the housing is used as an electrode. In addition, or instead of electrical isolation, the insulating layer 234 can be used to reduce an acoustic impedance mismatch between the flexible portion 250 of the housing 238 and the skin of the patient 230. The reduction in the acoustic impedance mismatch can allow the flexible portion 250 to more efficiently couple ultrasonic energy into the patient 230.

For example, the skin of the patient 230 and surrounding tissue can present a first acoustic impedance (e.g., related to a velocity of propagation of an acoustic wave within the body 230 medium). The flexible portion 250 of the housing 238 (e.g., a membrane), can present a second, different, acoustic impedance. In an example, the insulating layer 234 can be used to reduce an impedance mismatch between the first and second acoustic impedance, such as using an insulating layer having an intermediate acoustic impedance between the first and second acoustic impedances, such as a determined by a geometric mean or other function of the first and second acoustic impedances. In an example, the insulating layer can have a thickness of about a quarter-wavelength of the acoustic wavelength of the ultrasonic energy propagating through the insulating material, such as to reduce the acoustic impedance mismatch.

In an example, the insulating layer can include a polyurethane material, a polyimide or polyamide material, an epoxy material, a polyester-epoxy combination, or one or more other materials. In an example, the insulating layer 234 can include a conversion coating or one or more other electrochemically-applied coatings such as an oxide-forming hardcoat (e.g., for an aluminum housing 238). In an example, the insulating layer 234 can include a baked-on coating, such as epoxy coating, or an epoxy-polyester powder coating. In another example, the insulating layer 234 can be overmolded or painted onto at least a portion of the housing 238, such as on or near the exterior face of the flexible portion 250.

The local external assembly 214 can itself include a housing, separate from the housing 238 of the UT 216. In an example, the UT 216 can include an isolating mechanical coupling 236 between the housing 238 of the UT 216 and the housing of the local external assembly 214. For example, the isolating mechanical coupling 236 can help prevent or reduce unwanted buzzing or vibration of the local external assembly 214 during transmission by the UT 216. In an example, the isolating mechanical coupling 236 includes an elastomeric (e.g., rubber, silicone, etc.) sleeve, grommet, or gasket, such as located circumferentially around the housing 238 at or near where the housing 238 might contact the housing of the local external assembly 214. Similarly, one or more elastomeric washers can be used to mount the flange 240 of the housing 238 internally within the local external assembly 214, such as to reduce or prevent unwanted coupling of vibration internally.

FIG. 3 illustrates generally an example of a cut-away view of an ultrasonic transducer (UT) assembly 316, similar to the UT 216 of FIG. 2. The UT 316 of FIG. 3 includes a housing 338, including a mounting flange 340 and a flexible portion 350 (e.g., a flexible metallic membrane), coupled to a piezoelectric stack 346, the stack 346 attached to a printed circuit board (PCB) assembly 348 including a component mounting area 348A and a conductive portion 348B, and the attachment including using a first and a second lead tab 342-343.

In FIG. 3, a first, second, or a third component 347A-C (or other components) can be located on the component mounting area 348A, and one or more large components such as an inductor 344 can be mounted on an opposite side of the PCB assembly 348, such as to take advantage of otherwise unused volume within the housing 338. In an example, the PCB assembly 348 can include at least some components used to provide a matching circuit as discussed in FIGS. 2 and 4, such as including the inductor 344. For example, the inductor 344 is generally rated to withstand a voltage well in excess of the voltage applied during transmission of ultrasonic energy by the UT 316, such as a rating meeting or exceeding 200 Volts. Generally, the volume needed for the inductor 344 will increase as its maximum rated voltage increases, for a specified inductance. The inductor 344 can be located within a hollow portion of the housing 338. Locating the inductor within the housing 338 can provide transmission at a higher peak pressure than a transducer having a lesser-rated inductor, while also reducing the overall volume of the UT 316.

In FIG. 3, one or more cap screws such as a first cap screw 354A or a second cap screw 354B can be used to secure the PCB 348 to the housing 338, or to secure the UT 316 to another assembly (e.g., a housing of a local external assembly 214 such as shown in FIG. 2). In FIG. 3, an insulating layer 352 can be included between the piezoelectric stack 346 and the flexible portion 350 of the housing 338, such as to electrically isolate the piezoelectric stack 346 from the flexible portion 350 of the housing 338. Similar to FIG. 2, an insulating layer can be included on an exterior portion of the housing 338, such as on or near an exterior face of the flexible portion 350. However, the exterior face of the flexible portion 350 need not be insulated when the interior insulating layer 352 is used, since the interior insulating layer 352 can adequately prevent the housing 338 from becoming energized with a voltage applied when the UT 316 is transmitting. The interior insulating layer 352 can include an alumina disc or other material of slightly larger diameter than the rest of the piezoelectric stack 346, such as attached to the piezoelectric stack 346 prior to the installation within the housing 338 (as shown in FIG. 4).

In an example, the combination of the piezoelectric stack 346 and interior insulating layer 352 can be pre-fabricated, such as using similar adhesives or other materials or processing as the rest of the stack 346. In an example, one or more leads can be soldered or attached to one or more electrodes included in the stack 346, such as to connect the stack 346 to one or more matching components located on the PCB 348 (e.g., including the inductor 344 or one or more of the first, second, or third components 347A-C, etc.). The first and second lead tabs 342-343 can be used to simplify assembly as compared to using insulated lead wires, since the lead tabs 342-343 can be relatively rigid, and can penetrate the PCB 348 through one or more plated or non-plated holes. Such penetration can allow soldering or other electrical or mechanical bonding operations to be performed on or near the top-side component area 348A of the PCB 348 during assembly. In an example, one or more of the first tab 342 or the second tab 343 can be stamped, formed, or cut at the same time as one or more electrode layers included as a portion of the piezoelectric stack 346, such as shown in FIG. 4.

FIG. 4 illustrates generally an example of a portion of a piezoelectric transducer assembly 400 (such as the UT 216 or UT 316 of FIGS. 2-3), including a piezoelectric stack 446 and a matching circuit 462. The stack 446 of FIG. 4 can be used with the ultrasonic transducer housing of FIG. 2-3, or 5A-C, such as for bi-directional wireless information transfer as a unimorph flexural transducer. In a unimorph example, the piezoelectric stack 446 can use an extensional/contractional mode of operation that excites or detects flexural motion by an attached flexible non-piezoelectric substrate (e.g., the flexible portions 250 or 350 of FIGS. 2-3). In the example of FIG. 4, the stack can include multiple layers of a piezoelectric material, such as a piezoelectric crystal, a piezoceramic, a piezocomposite, or a piezopolymer material. Examples of piezopolymer material include poled polyvinylidene fluoride (PVDF), a fluoropolymer film, among others. Examples of a piezoelectric crystal material include lead magnesium niobate-lead titanate (PMN-PT), among others. Examples of piezocomposite materials include epoxy-loaded or other polymer-loaded piezoceramic materials, among others. Examples of a piezoceramic material include lead zirconate titanate (PZT), among others.

In FIG. 4, a first piezo layer 458A can be attached to a first electrode layer 456A, connected to a first lead 442. In an example, the opposite side of the first piezo layer 458A can be attached to a second electrode layer 456B, connected to a second lead 443. In FIG. 4, a second piezo layer 458B, such as having an opposite polarization (e.g., indicated by an arrow in FIG. 4) can also be connected to the second electrode layer 456B. Similarly, a third piezo layer 458C, a third electrode layer 456C, and a fourth electrode layer 456D can be attached and connected as shown in FIG. 4. FIG. 4 shows a parallel connection example, but in another example, a series configuration can be used, and the polarization of each piezo layer 458A-C need not be opposed.

In FIG. 4, each of the first through third piezo layers 458A-C can include a disc of piezoceramic lead zirconate titanate (PZT) material, such as PIC-255 provided by PI Ceramic (Germany). For example, each piezoceramic disc can be approximately 10 mm in diameter, and approximately 0.25 mm in height. In FIG. 4, one or more of the first through fourth electrode layers 456A-D can include a copper electrode, or other conductive material, bonded to the adjacent piezo layers using a conductive adhesive, such as a conductive structural adhesive (e.g., epoxy, or one or more other adhesives). For example, one or more of the electrode layers 456A-D can include one or more holes, such as a hole 460, to allow a single adhesive application to bond both faces of a respective electrode layer (e.g., the second electrode layer 456B) to respective adjacent piezo layers (e.g., the first and second piezo layers 458A-B), forming a relatively durable unitized assembly.

In an example, similar to the stack 346 of FIG. 3, an insulating layer 452 can be attached to the fourth electrode layer 456D. For example, the insulating layer 452 can include alumina, and can be approximately 12 mm in diameter, and approximately 0.25 mm in height, such as to electrically isolate the stack 446 from an adjacent conductive housing. Alumina can be desirable because of its rigidity and electrical isolation properties (e.g., a relatively high dielectric breakdown voltage as compared to some other non-ceramic materials). For example, the rigidity and thinness of the alumina when used as the insulating layer 452 can allow relatively efficient mechanical coupling of acoustic energy between the stack 446 and housing at ultrasonic frequencies, such as a resonant frequency of the whole UT assembly including the piezoelectric stack 446, the housing, and the insulating layer 452, while still providing desirable high-voltage isolation. In an example, as discussed in FIG. 3, the insulating layer 452 can be assembled with the rest of the stack 446 prior to installation within the housing, such as using an adhesive similar to the adhesive used for bonding together one or more other layers of the stack 446.

In an example, one or more of the second or third piezo layers 458B-C can be omitted. However, use of more piezo layers in a parallel configuration and assembled having opposing polarizations as shown in FIG. 4 can provide a greater pressure per volt of input stimulus as compared to a piezoelectric stack 446 including fewer layers. In an example, the insulating layer 452 can be omitted, along with the fourth electrode layer 456D. Instead, the stack 446 can be attached to a conductive portion of the housing (e.g., the flexible portion 250, 350, or 550 of the housing of FIG. 2-3, or 5), and the conductive portion can be used as an electrode. Use of the housing as an electrode can simplify the assembly of the stack 446, but at the cost of adding an insulating layer elsewhere, such as to isolate the user of the transducer assembly from voltages used to excite the stack 446 when transmitting ultrasonic energy.

In FIG. 4, a matching circuit 462 can be connected to the first and second leads 442 and 443 as discussed in FIG. 2, such as to modify an admittance characteristic of the piezoelectric stack 446. In FIG. 4, a first resistor 447A can be connected to an inductor 444, shunted by a capacitor 449 in series with a second resistor 447B. In an example, the stack 446 can be modeled as a series-resonant circuit when the stack 446 is receiving ultrasonic energy and providing a time-varying charge output to a charge amplifier circuit through the matching circuit 462.

Figure 5C:
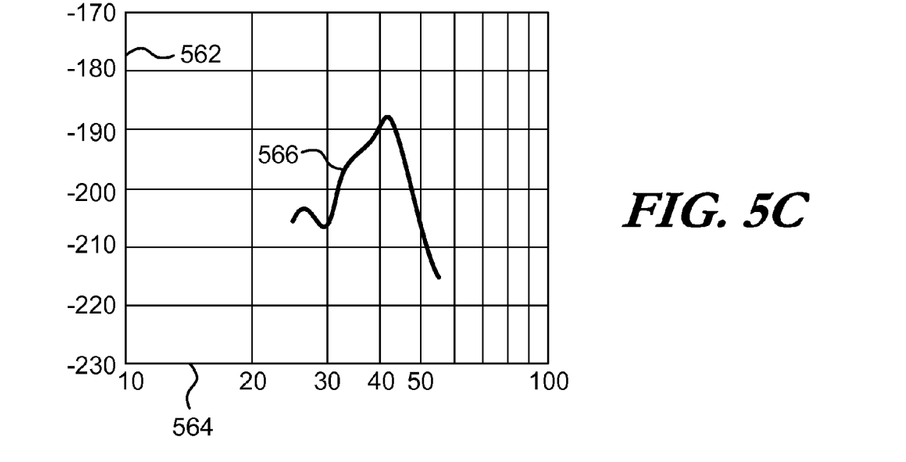

FIGS. 5A-C include illustrative examples of an ultrasonic transducer housing 500 (e.g., the housing 238 or 338 discussed in FIGS. 2-3) including an upper portion 538A and a lower portion 538B, a finite element model of a portion of the housing 500 including a piezoelectric element 546 illustrating deformation of a flexible portion 550 of the housing 500, and an illustrative example of a receiving sensitivity plot 566 corresponding to the housing 500 of FIGS. 5A-C.

While other dimensions can be used, in the illustrative examples of FIGS. 5A-C, the housing 500 can include a stainless steel housing (e.g., including surgical-grade stainless steel such as austenitic grade 316 stainless steel or another grade or type of stainless steel) having an overall exterior height of approximately 12.2 mm. The upper flange thickness can be about 1.5 mm thick, and an overall height of the upper portion 538A can be around 7.1 mm thick, when measured from the exterior. The overall exterior diameter of the flange 540 can be about 30 mm. The overall outer diameter of the upper portion 538A can be about 24 mm, and the overall outer diameter of the lower portion 538B can be about 16.5 mm, such as including a tapered or radiused portion leading down to an exterior bottom face of the flexible portion 550. The inner diameter of the upper portion 538A can be about 18.2 mm, and the inner diameter of the lower portion 538B can be about 13.2 mm. The thickness of the flexible portion 550 not including the piezoelectric element 546 can be about 1.2 mm. The thickness of the flexible portion 550 and the piezoelectric element 546 can vary, depending on the number of layers used in the piezoelectric element, and whether or not one or more insulating layers are used either internally or externally to the housing 500 (e.g., as shown in FIGS. 2-4). In an example, the combined thickness of the flexible portion 550 and the element 546 can be less than or equal to 2 mm.

In the illustrative examples of FIGS. 5A-C, an ultrasound transducer can use the combination of the housing 500 and piezoelectric element 546 to provide a unimorph flexural transducer as discussed in FIGS. 2-3. For example, extension or contraction of the element 546 can be converted into flexure of the flexible portion 550, or vice versa, (e.g., the flexible portion 550 can be a mechanical membrane to couple acoustic energy to or from the element 546), as shown in FIG. 5B. Such conversion of extension or contraction to flexural motion can occur since the element 546 (e.g., the stack 246, 346, or 446 of FIGS. 2-4) is fixed to the flexible portion 550 and located asymmetrically to a neutral plane of the flexible portion 550 of the housing.

In an illustrative example of an ultrasonic transducer such as using the matching circuit as discussed in FIGS. 2-4 and housing geometry of FIGS. 5A-C, the transmit sensitivity of the ultrasound transducer can meet or exceed about 250 kilo-Pascals per Volt at a distance of 0.2 meters using water as a propagation medium, when operated in a voltage-driven mode, corresponding to a transmitting voltage response (TVR) meeting or exceeding 156 Decibels per Volt at a distance of 1 meter using water as a propagation medium, (relative to 1 microPascal per Volt at a distance of 1 meter).

In an illustrative example of an ultrasonic transducer such as using the matching circuit as discussed in FIGS. 2-4 and housing geometry of FIGS. 5A-C, the receiving sensitivity meeting or exceeding about 3 picoCoulombs per Pascal (e.g., using a charge-mode of receiving such as coupled to a charge amplifier as discussed in FIG. 2), and providing a total static capacitance less than or equal to approximately 20 nanoFarads. For example, FIG. 5C shows a free-field receive sensitivity 566 as a function of frequency 564 (plotted in kHz), and represented in decibels (562), relative to 1 microPascal per Volt.

Finite element modeling (FEM) can be used to model a portion of the housing 500, such as to explore variations in one or more housing 500 parameters (e.g. diameter, thickness, material selection, etc.), such as to reduce or eliminate unwanted spurious responses (e.g., unwanted resonances, or the like) in the transmitting or receiving characteristics, such as to obtain one or more of the deformation model of FIG. 5B or the receiving characteristic of FIG. 5C (e.g., to achieve a specified determinable peak efficiency at or near a specified frequency).

Figure 6:
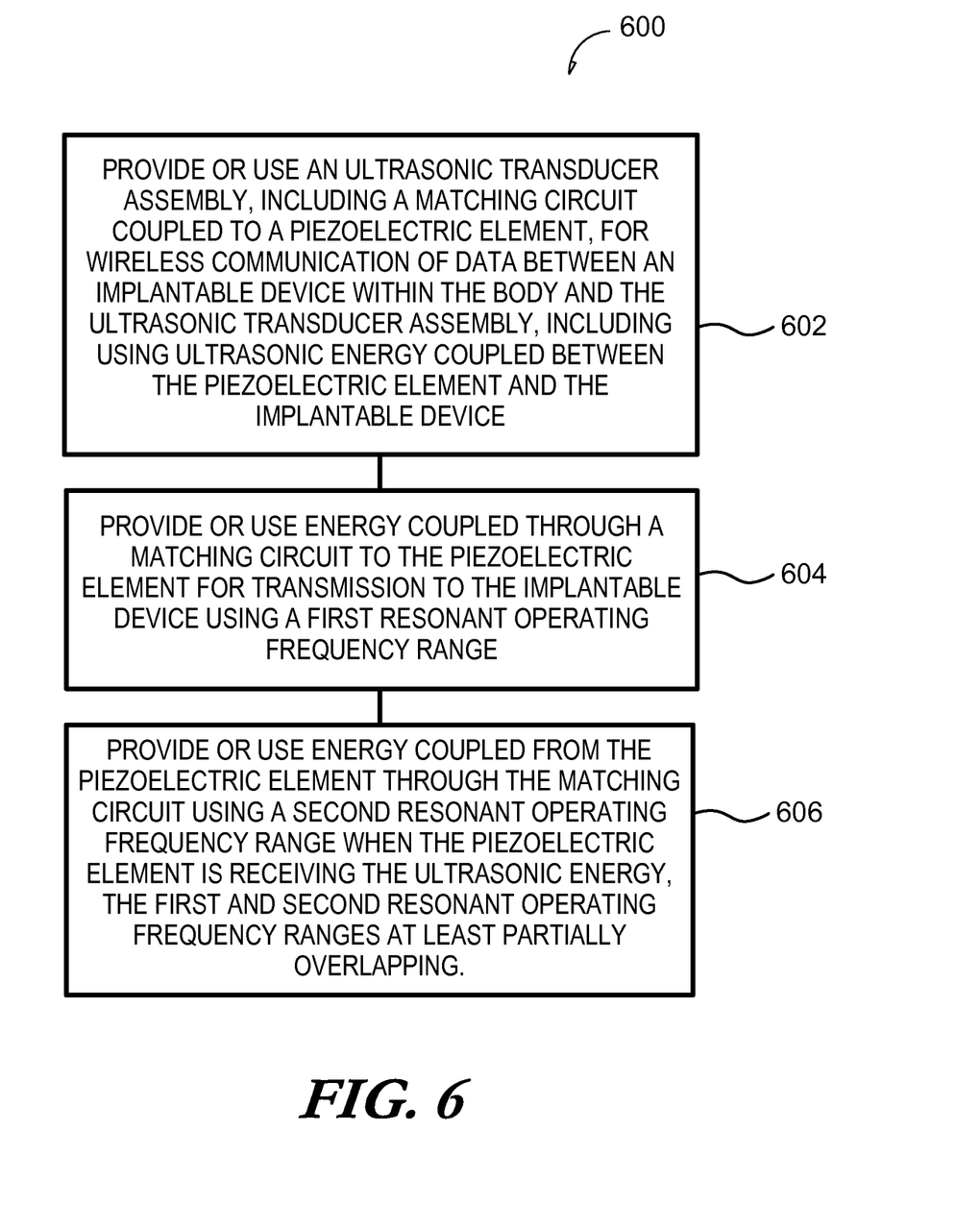
FIG. 6 illustrates generally a method including providing or using an ultrasonic transducer assembly.

FIG. 6 illustrates generally an example 600 including providing or using an ultrasonic transducer assembly, such as including one or more of the piezoelectric assemblies discussed in FIGS. 1-4, and 5A-C.

At 602, an ultrasonic transducer assembly (e.g., one or more of UTs 116, 216, or 316 of FIGS. 1-3) can be provided or used for wireless communication of data between an implantable device within the body and the ultrasonic transducer assembly, the ultrasonic transducer assembly including a matching circuit coupled to a piezoelectric element.

At 604, ultrasonic energy can be provided or used by coupling the energy through the matching circuit to the piezoelectric element using a first resonant operating frequency range.

At 606, ultrasonic energy can be provide or used by coupling the energy through the matching circuit from the piezoelectric element, when the piezoelectric element is receiving, using a second resonant operating frequency range. In an example, the first and second resonant operating frequency ranges can at least partially overlap, such as discussed in FIGS. 2-3.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile tangible computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of The claimed invention is:

1. An ultrasonic transducer assembly comprising:
   a housing including a flexible portion, the flexible portion configured to contact skin of a body containing an implantable device;
   a piezoelectric element within the housing configured for wireless communication of data between the implantable device and the ultrasonic transducer assembly using ultrasonic energy coupled to the flexible portion of the housing;
   a matching circuit included at least partially within the housing;
   wherein the matching circuit is configured to provide energy to the piezoelectric element using a first resonant operating frequency range, and to receive energy from the piezoelectric element using a second resonant operating frequency range when the piezoelectric element is receiving ultrasonic energy; and
   wherein the first and second resonant operating frequency ranges are at least partially overlapping.

2. The ultrasonic transducer assembly of claim 1, wherein the piezoelectric element is configured to operate in a voltage-driven mode when the piezoelectric element is providing ultrasonic energy; and
   wherein the piezoelectric element is configured to provide a charge output to drive a charge amplifier when the piezoelectric element is receiving ultrasonic energy.

3. The ultrasonic transducer assembly of claim 1, wherein the piezoelectric element is configured to at least one of provide or receive the ultrasonic energy using a flexural vibration mode of the flexible portion of the housing.

4. The ultrasonic transducer assembly of claim 3, wherein the piezoelectric element includes a circular footprint; and wherein the flexural vibration mode of the flexible housing includes a deformation component orthogonal to a face of the circular footprint.

5. The ultrasonic transducer assembly of claim 1, wherein the first and second resonant operating frequency ranges each include a like frequency of determinable efficiency between 20 kHz and 800 kHz.

6. The ultrasonic transducer assembly of claim 5, wherein the first and second resonant operating frequency ranges each include a like frequency of peak efficiency at about 40 kHz.

7. The ultrasonic transducer assembly of claim 1, wherein the housing includes one of aluminum or stainless steel.

8. The ultrasonic transducer assembly of claim 1, wherein the housing includes an insulating layer on the flexible portion.

9. The ultrasonic transducer assembly of claim 8, wherein the insulating layer is located on an exterior face of the flexible portion.

10. The ultrasonic transducer assembly of claim 9, wherein the insulating layer is configured to decrease an acoustic impedance mismatch between the ultrasonic transducer assembly and the body in contact with the flexible portion of the ultrasonic transducer assembly in one or more of the first or second resonant operating frequency ranges.

11. The ultrasonic transducer assembly of claim 9, wherein at least a portion of the housing is electrically coupled to a portion of the piezoelectric element and wherein at least a portion of the housing is electrically coupled to the matching circuit.

12. The ultrasonic transducer assembly of claim 8, wherein the insulating layer is located on an interior face of the flexible portion and is configured to electrically isolate the flexible portion of the housing from the piezoelectric element.

13. A method, comprising:
   providing or using an ultrasonic transducer assembly, including a matching circuit coupled to a piezoelectric element, for wireless communication of data between an implantable device within the body and the ultrasonic transducer assembly, the providing including using ultrasonic energy coupled between the piezoelectric element and the implantable device;
   providing or using energy coupled through a matching circuit to the piezoelectric element for transmission to the implantable device using a first resonant operating frequency range;
   providing or using energy coupled from the piezoelectric element through the matching circuit using a second resonant operating frequency range when the piezoelectric element is receiving the ultrasonic energy; and
   wherein first and second resonant operating frequency ranges are at least partially overlapping.

14. The method of claim 13, comprising at least one of providing a charge output when the piezoelectric element is receiving ultrasonic energy or providing ultrasonic energy using the piezoelectric element operating in a voltage-driven mode.

15. The method of claim 13, comprising at least one of providing or receiving ultrasonic energy using a flexural vibration mode of a flexible portion of a housing coupled to the piezoelectric element.

16. The method of claim 13, wherein the first and second resonant operating frequency ranges each include a like frequency of determinable efficiency between 20 kHz and 800 kHz.

17. The ultrasonic transducer assembly of claim 16, wherein the first and second resonant operating frequency ranges each include a like frequency of peak efficiency at about 40 kHz.

18. The method of claim 13, comprising providing or using an insulating layer on a flexible portion of a housing of the ultrasonic transducer assembly; and
   wherein the flexible portion is configured to contact skin of the body containing the implantable device.

19. The method of claim 17, wherein the providing or using the insulating layer includes providing or using an insulating layer on an exterior face of the flexible portion of the housing;
   wherein the body provides a first acoustic impedance and the ultrasonic transducer assembly provides a second acoustic impedance; and
   wherein the providing or using the insulating layer includes decreasing an impedance mismatch between the first and second acoustic impedances at least in part using the insulating layer.

20. The method of claim 17, wherein the electrically insulating comprises providing an insulating layer on an interior face of the flexible portion of the housing to electrically isolate the piezoelectric element from the flexible portion of the housing.

* * * * *